United States Patent [19]

Schmidt

[11] Patent Number: 5,049,149
[45] Date of Patent: Sep. 17, 1991

[54] SAWING GAUGE SYSTEM

[76] Inventor: Joachim Schmidt, Mohnweg 18, D-5000 Cologne 40, Fed. Rep. of Germany

[21] Appl. No.: 448,094

[22] Filed: Dec. 12, 1989

[30] Foreign Application Priority Data

Dec. 14, 1988 [DE] Fed. Rep. of Germany ....... 3842645

[51] Int. Cl.⁵ .............................................. A61N 1/30
[52] U.S. Cl. ........................................ 606/87; 606/89; 606/88
[58] Field of Search ...................... 606/87, 89, 79, 102, 606/96, 82, 88

[56] References Cited

U.S. PATENT DOCUMENTS

| 2,547,571 | 6/1950 | Ettinger | 606/96 |
| 4,718,413 | 1/1988 | Johnson | 606/96 |
| 4,926,847 | 5/1990 | Luckman | 606/88 |

FOREIGN PATENT DOCUMENTS 3211153 9/1983 Fed. Rep. of Germany .
511016 9/1971 Switzerland .
8701579 3/1987 World Int. Prop. O. .

Primary Examiner—Robert A. Hafer
Assistant Examiner—David Kenealy
Attorney, Agent, or Firm—Spencer & Frank

[57] ABSTRACT

A sawing gauge system to be used in case of intertrochantery accommodation osteotomies includes a first sawing gauge having an underside curved like a hollow cylinder for a face-to-face engagement with the bone surface of the femur shaft and a sawing opening oriented vertical to the axis of the femur shaft; and a second sawing gauge having an underside being curved like a hollow cylinder for a face-to-face engagement with the bone surface of the femur shaft and a sawing opening inclined towards the sawing opening in the first sawing gauge by an angle of 6° if the axes of the undersides of the first and second sawing gauges coincide.

10 Claims, 5 Drawing Sheets

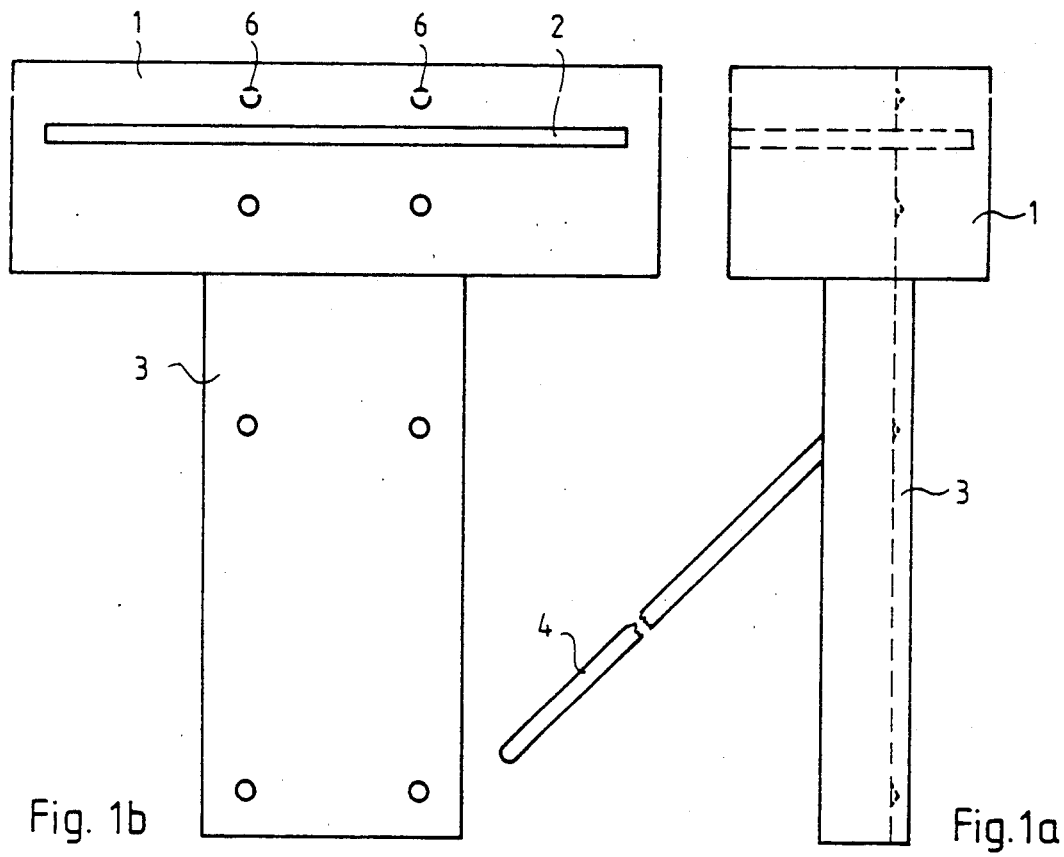
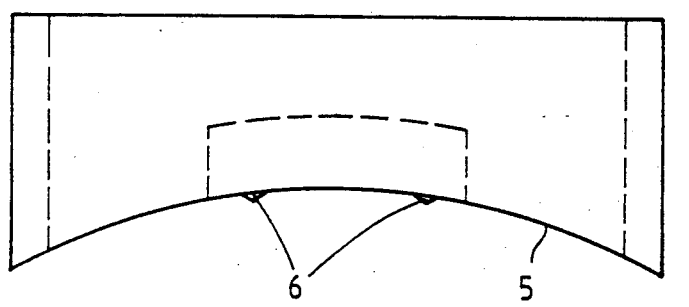
Fig. 1b  Fig. 1a  Fig. 1c

SAWING GAUGE SYSTEM

CROSS REFERENCE TO RELATED APPLICATION

This application claims the priority of the Federal Republic of Germany application No. P 38 42 645.5 filed Dec. 14th, 1988, which is incorporated herein by reference.

BACKGROUND OF THE INVENTION

The present invention relates to a sawing gauge system to be used in case of intertrochantery accommodation osteotomies.

The large spongeous bone area available during intertrochantery accomodation osteotomies would suggest that a good reformatiom of the bone structure can be achieved. It still, however, can occur that the bone only heals slowly due to bone reabsorption in the osteotomy area. The bone reabsorption takes place as a result of micromovements on the contact surface and signalizes an insufficient interfragmentary compression.

The compression of the bone fragments is usually carried out with an angle plate aided by a plate clamp or according to the slotted slide plate principle. These methods cause the lateral cortical to be compressed as the plate is excentrically situated. The medial cortical is, on the other hand, under tension. In general, the principle of overbending of the plate is not taken into consideration. It is therefore a tension chord osteosynthesis.

There are numerous literature references as to how interfragmentary compression can be achieved during intertrochantery osteotomy. Following the method according to Buchner, the compression is achieved whilst the plate is being struck in due to an increasing distance between the razor socket and the osteotomy area. The renewed striking of the plate previously fixed in relation to the distal pressurizes the osteotomy area. In this connection, reference is made to an article in the journal "Orthopädie" No. 112 by G. M. Russ, published in 1974, pages 348–350. In another reference, "Die intertrochantere Osteotomie bei Coxarthrose" (Intertrochatery osteotomy by coxarthrosis) by R. Schneider published in 1979 by Sprinqer-Verlag, Berlin, the author recommends inclined osteotomy areas which then become compressed by screwing the proximal screw. In another reference, an article in the journal "Orthopä die" No. 122, published in 1984, pages 705–715, Heisel suggests that the principle of overbending of the plate according to Bagby be taken into consideration in order to prevent the osteotomy from splitting open on the medial side. Bagby describes the overbending of the plate in the case of shaft fractures. All these methods have the disadvantage, that their effectiveness cannot be assessed acurately and that some can cause considerable shear stressing.

SUMMARY OF THE INVENTION

It is an object of the invention to provide a device which can remove a wedge-shape section of bone with a predetermined wedge-angle so that an optimal prestress load F can act.

The object and others to become apparent as the specification progresses, are accomplished by the invention, according to which, briefly stated, the sawing gauge system to be used in case of intertrochantery accommodation osteotomies includes a first sawing gauge having an underside curved like a hollow cylinder for a face-to-face engagement with the bone surface of the femur shaft and a sawing opening oriented perpendicularly to the axis of the femur shaft; and a second sawing gauge having an underside being curved like a hollow cylinder for a face-to-face engagement with the bone surface of the femur shaft and a sawing opening inclined towards the sawing opening in the first sawing gauge by an angle of 6° if the axes of the undersides of the first and second sawing gauges coincide.

The sawing gauge system according to the invention consists of two seperate sawing gauges enabling two cuts to be carried out quickly and accurately. The first cut is made perpendicularly to the shaft axis in the proximal femur and then the second cut is made at an angle, in particular a 6° angle, to the first cut, the second cut intersecting the first cut. The second sawing gauge can be positioned exactly in relation to the position of the first cut.

The optimal reformation of the osteotomy requires an optimal interfragmentary pressure distribution. This goal can be achieved by precisely defining and therefore quantifing an angle a in degrees so that an exact opening in the lateral direction of the osteotomy surfaces is defined. The wedge-shape section of bone which has to be removed for correction is dimensioned in such a way that the opening in the lateral direction remains open after correction and prior to the prestressing. This means that the removed varisation wedge is smaller by $\alpha$ and the valgisation wedge is greater by a. In this way the medical corticalis is the first to be pressurized at the beginning of the prestressing with load F. By utilising the elastic and biomechanical properties of the angle-plate the proximal fragment tilts about a pivot in the medial corticalis as the prestressing continues and does so until the opening is closed and an even medial and lateral compression has been reached. This movement prevents shear stress from taking place.

The results of experiments show that not only when at rest, but also when static loading is simulated, an even interfragmentary compression distribution can be obtained during intertrochantery accomodation osteotomies if the osteotomy areas are opened at an angle of $\alpha = 6°$ prior to prestressing with a load F = 1000 N. The priciple of tension chord osteosynthesis is optimated by the principle of compressional osteosynthesis. Tensional stresses and stress peaks which result in the pathological reduction of bone material are reduced. Relative movements can be avoided.

The angle of $\alpha = 6°$ can be unproblematically implemented using two sawing gauges during an operation. The bone is precisely cut perpendicular to the distal fragment with the first sawing gauge. Then the plate-positioning instrument is struck into the thigh shaft at an angle which is 6° smaller than the actual angle required for the correction due to the plate bending upwards during the prestressing i.e it valgarises. After the angle-plate has been positioned a second saw gauge is attached to the plate-shaft. This makes it possible to remove a correction wedge from the proximal fragment whilst at the same time taking the angle $\alpha = 6°$ into consideration. The sawing direction runs perpendicularly to the plate-shaft minus 6°. In that way a lateral opening of the osteotomy areas of 6° remains. The plate is then firmly fixed to the thigh shaft by a screw through the uppermost slot and is tightened with a plate tightener. The final stages of the assembly are the usual ones.

The sawing gauges have concave curved undersides and these guarantee that they can be exactly fitted to the femur shaft. Metal pins which dig into the periost and/or Rändelschrauben shaped as set-screws are used to prevent movement.

The length of the contact surface area and in particular that of the first sawing gauge is limited by the size of the operation wound. It is nevertheless large enough for the parallel assembly if the length of the contact surface area is longer than the length of the cut to be sawed. The first sawing gauge is manually held with a grip.

The second sawing gauge is pushed onto the shaft of the angle-plate with a slide part and locked in the preferred embodiment with a knurled adjusting screw (Rändelschraube) after the angle-plate has been mounted. A sawing block with a sawing opening is connected to a longitudinally adjustable and preferably lockable part which is connected to the slide part by being attached to a knee part. The direction of movement of the slide part and the longitudinally adjustable part are vertically on top of one another. This means that the second sawing gauge can be exactly positioned in front of the cut made by the first sawing gauge. The knee part between the height adjustable part and the sawing block leads to the contact surface area of the second sawing gauge with the femur shaft being turned exactly 90° away from the contact surface area of the angle-plate shaft. The sawing direction is, in accordance with the sawing opening, cut into the sawing block $90° - 6° = 84°$ from the femur shaft, so that a correction wedge can be removed from the proximal fragment and a lateral opening of the osteotomy areas of 6° remains.

The utilisation of the sawing gauge system according to the invention leads to less forming of pseudarthrosis and less slower healing of the bone as well as greater safety with regard to post operative exercises and mobilisation of the patient as this is a strong osteosynthesis.

BRIEF DESCRIPTION OF THE DRAWINGS

FIG. 1a is a schematic side elevational view of a preferred embodiment of the first sawing gauge.

FIG. 1b is a view of the underside to be placed on the femur shaft of the first sawing gauge according to FIG. 1a.

FIG. 1c is a front elevation of the first saw gauge according to FIG. 1a.

FIG. 2b is a plan elevation of the second sawing gauge according to FIG. 2a.

FIG. 2c is a front elevation of the second saw gauge according to FIG. 2a.

DESCRIPTION OF THE PREFERRED EMBODIMENT

Figure 1D:
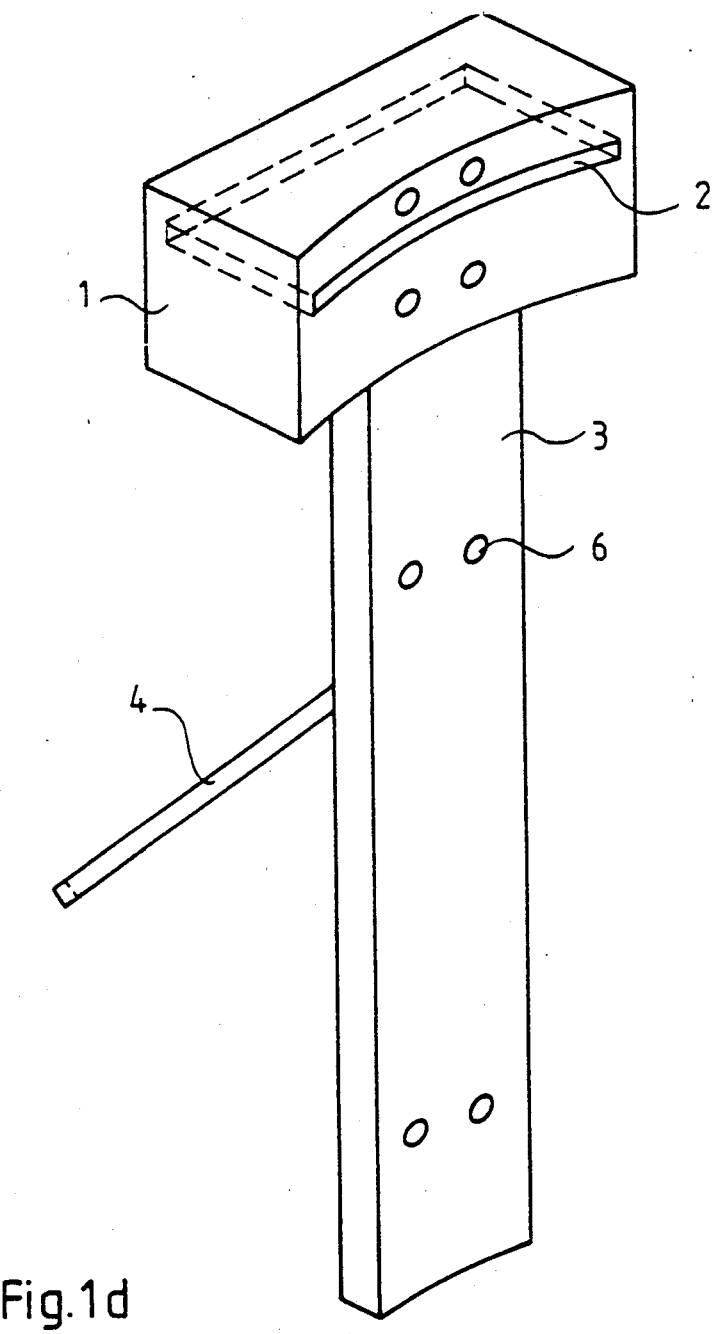
FIG. 1d is a perspective view of the first saw gauge according to FIGS. 1a to 1c.
Figure 2B:
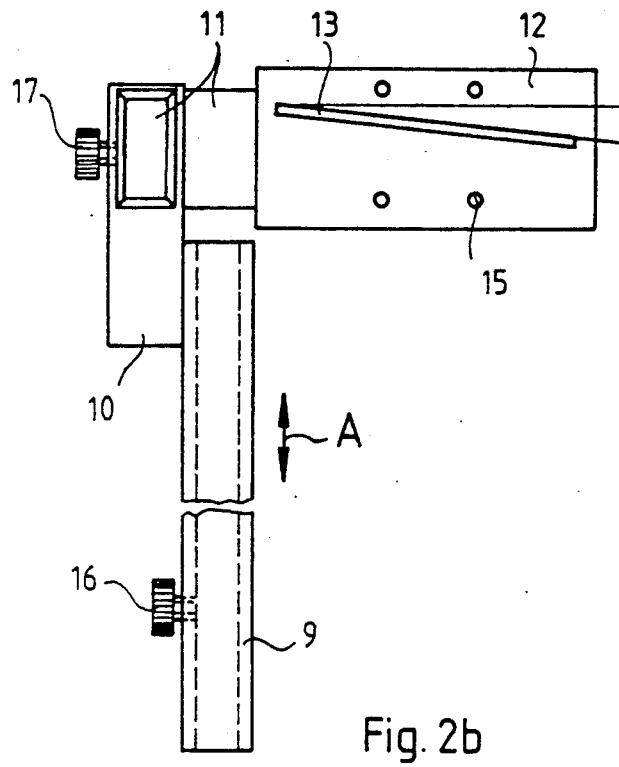
Figure 2A:
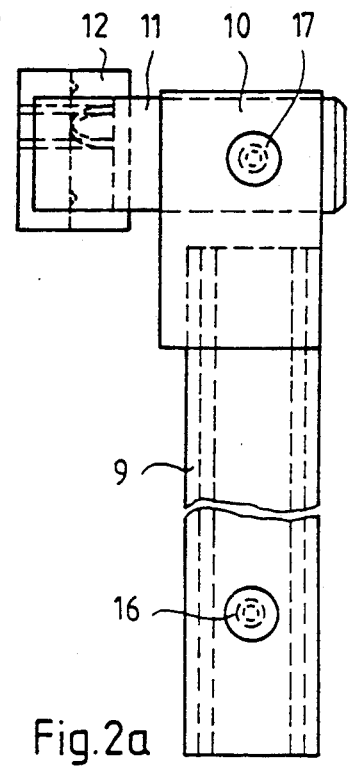
FIG. 2a is a schematic side elevational view of a preferred embodiment of the second sawing gauge.
Figure 2C:
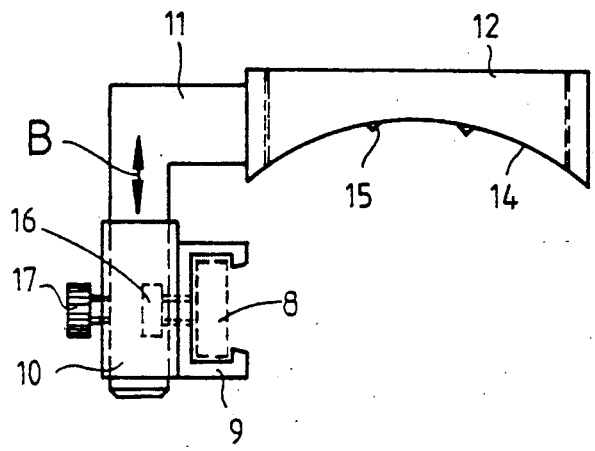
Figure 2D:
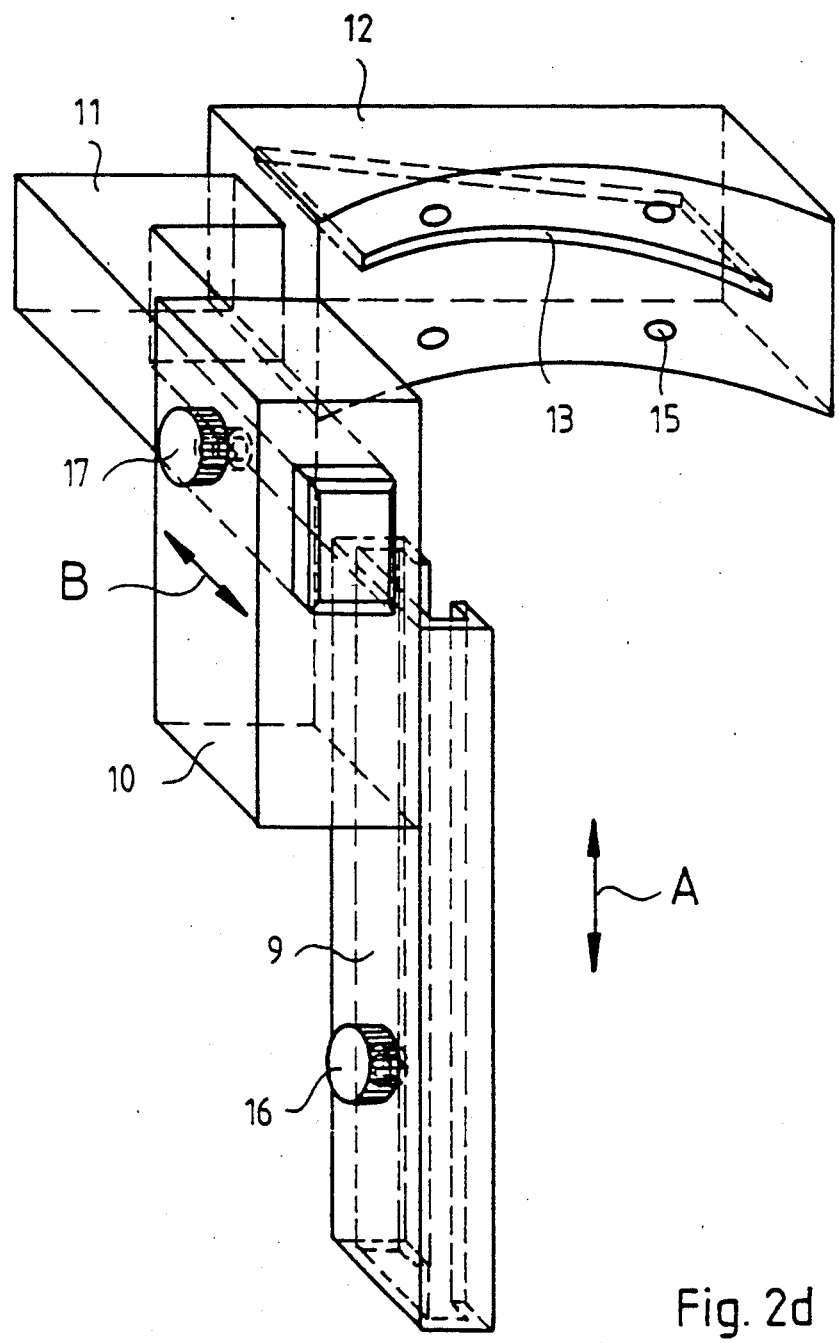
FIG. 2d is a perspective view of the second saw gauge according to FIGS. 2a to 2c.

The experimentally determined optimal wedge angle of $\alpha = 6°$ can be set easily during an operation with two sawing gauges that are installed one after the other. The femur is cut exactly (i.e. perpendicularly) to its shaft axis with the first sawing gauge. The preferred embodiment of the first sawing gauge, as illustrated in different views in the FIGS. 1a to 1d, consists of a sawing block 1 with a sawing opening 2, a support 3 and a handle 4, whereby the sawing opening 2 is exactly perpendicular to the longitudinal direction of support 3 which implies that it is, in turn, cut into the sawing block 1 perpendicular to the shaft axis. The support 3 is curved on its underside in the form of a hollow cylinder and is therefore similar in shape to that of the bone. In order to ensure that the support 3 is protected against non-intentional movements along the bone surface when leaning against the bone the support is evenly covered with metal pins 6 on the underside 5 which dig into the periost. The support 3 supports the sawing block 1 and the sawing opening 2. The handle 4 which is mounted on the upper side of the support 3 enables the first sawing block to be held manually to prevent sliding during the sawing process.

Figures 3A, 3B:
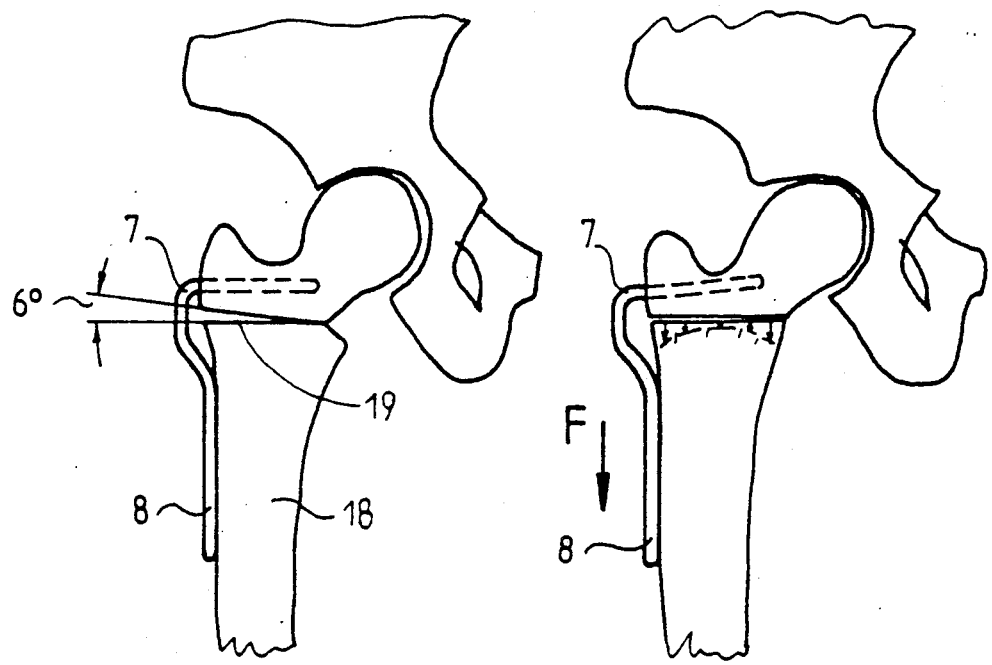
FIG. 3a shows the osteotomy angle prior to compression.
FIG. 3b shows the interfragmentary compression distribution in the case of a osteotomical angle of 6°.

After the bone has been separated, whereby the sawing opening 2 acts as a stencil, the first sawing gauge is removed and a plate-positioning instrument is struck into the thigh shaft at an angle which is 6° smaller than the actual angle required for the correction because—as can be seen from the FIGS. 3a and 3b—an angle plate 7 yet to be positioned bends up by 6° during the prestressing.

A second sawing gauge is attached to the plate-shaft 8 of the angle-plate 7 after it has been positioned.

The preferred embodiment of the second sawing gauge, as illustrated in different views in the FIGS. 2a to 2d, is needed to remove the wedge-shape section of bone with a wedge-angle of 6°. The second sawing gauge differs from the first sawing gauge in the way that it is positioned and the position of its sawing opening. The second sawing gauge consists of a slide part 9, which can be pushed onto the angle plate shaft 8 (as illustrated dashed in FIG. 2c) of the angle plate 7 in the direction of arrow A, a longitudinally, in the direction of arrow B adjustable part 10, a knee part 11 and a sawing block 12 with a sawing opening 13 situated at an angle. The underside 14 of the sawing block 12, which is to lean against the bone surface, is formed like a hollow cylinder and is covered with a number of metal pins 15 to augment the adhesion.

The slide part 9 is connected to the longitudinally adjustable part 10 in such a way that they can be moved vertically relative to each other and also that the slide part 9 can be moved vertically relative to the first osteotomy cut made by the first sawing gauge. The right-angled knee part 11 is connected to the longitudinally adjustable part 10 and the sawing block 12. As the sawing block 12 is connected to the knee part 11 it can be lowered to rest on the bone by moving the longitudinally adjustable part 10 and can be moved laterally by moving the slide part 9 along the plate-shaft 8 of the angle-plate 7 until the sawing opening 13 of the sawing block 12 is exactly lined up with the existing osteotomy cut. The relative positioning of the slide part 9 and the plate-shaft 8 is fixed with a gerändelte or knurled set-screw 16. Another gerändelte set-screw 17 is used to fix the longitudinally adjustable part 10 to the knee part 11.

The correction wedge is removed from the proximal fragment. The sawing direction is at an angle of $90° - 6° = 84°$ to the angle plate-shaft 8. A lateral opening of the osteotomy areas of 6° remains.

The FIGS. 3a and 3b illustrate the effect of compression on the fissure 19 cut into the femur 18 using the sawing gauges according to the invention. The angleplate 7 and the plate-shaft 8 are fixed with a screw through the upper (not shown) slot. Using an ordinary plate tightener (also not shown) the bones are then transferred from the position as illustrated in FIG. 3a with the open fissure to the position as illustrated in FIG. 3b with the closed fissure. The prestressing load is approximately 1000 N The final stages of fixation are the usual ones. The stressing device is not part of the invention. FIGS. 3a and 3b are only meant to show the surgical method used when utilising the sawing gauges according to this invention in order to be able to clarify their function.

It will be understood that the above description of the present invention is susceptible to various modifications, changes and adaptations, and the same are intended to be comprehended within the meaning and range of equivalents of the appended claims.

What is claimed is:

1. A sawing gauge system to be used for intertrochantery accommodation osteotomies for removing a wedge-shaped section of bone, comprising
   (a) a first sawing gauge having an underside; said underside being curved like a hollow cylinder for a face-to-face engagement with the bone surface of a femur shaft;
   (b) a first sawing opening provided in said first sawing gauge; the first sawing opening being oriented perpendicularly to the axis of the femur shaft when said underside of said first sawing gauge is in face-to-face engagement with the bone surface of the femur shaft;
   (c) a second sawing gauge having an underside; said underside being curved like a hollow cylinder for a face-to-face engagement with the bone surface of the femur shaft;
   (d) a second sawing opening provided in said second sawing gauge; the second sawing opening being oriented to form an angle of 6° with a perpendicular to the axis of the femur shaft when said second sawing gauge is in face-to-face contact with the bone surface of the femur shaft.

2. A sawing gauge system as defined in claim 1, wherein said undersides of the first and second sawing gauges have metal pins attached to them.

3. A sawing gauge system as defined in claim 1, wherein said first sawing gauge has a contact area with the bone surface of the femur shaft which is greater than the area of said first sawing opening as defined by the contact area with the bone surface of said first sawing gauge, and said first sawing opening is disposed adjacent the bone surface of the femur shaft when the first sawing gauge is in face-to-face engagement with the bone surface of a femur shaft.

4. A sawing gauge system as defined in claim 1, wherein said first sawing gauge comprises a handle.

5. A sawing gauge system as defined in claim 1, wherein said second sawing gauge comprises an angle plate having a shaft and a longitudinally adjustable slide part which can be attached to the shaft of said angle plate; whereby
   (a) the orientation of a contact area of said second sawing gauge and the plane of said angle plate are substantially perpendicular in relation to each other; and
   (b) the orientation of the axis of said underside curved like a hollow cylinder of the second sawing gauge and the direction of elongation of said angle plate run approximately parallel to each other.

6. A sawing gauge system as defined in claim 5, further comprising a telescopic part and a longitudinally adjustable part disposed between said second sawing gauge and said angle plate, said telescopic part and said longitudinally adjustable part being movable relative to each other, wherein the distance between said angle plate and the axis of said underside curved like a hollow cylinder of the second sawing gauge can be set by either one of said telescopic part and said longitudinally adjustable part.

7. A sawing gauge system as defined in claim 5, wherein said angle plate comprises an element to lock said slide part.

8. A sawing gauge system as defined in claim 5, wherein said longitudinally adjustable part comprises an element to lock said slide part.

9. A sawing gauge system as defined in claim 5, wherein both said angle plate and said longitudinally adjustable part comprise an element to lock said slide part.

10. A sawing gauge system as defined in claim 7, wherein said element to lock said slide part comprises at least one set-screw.

* * * * *